(12) United States Patent
Pantaleoni et al.

(10) Patent No.: US 8,943,091 B2
(45) Date of Patent: Jan. 27, 2015

(54) SYSTEM, METHOD, AND COMPUTER PROGRAM PRODUCT FOR PERFORMING A STRING SEARCH

(71) Applicant: NVIDIA Corporation, Santa Clara, CA (US)

(72) Inventors: Jacopo Pantaleoni, Berlin (DE); David Tarjan, Santa Clara, CA (US)

(73) Assignee: NVIDIA Corporation, Santa Clara, CA (US)

( * ) Notice: Subject to any disclaimer, the term of this patent is extended or adjusted under 35 U.S.C. 154(b) by 142 days.

(21) Appl. No.: 13/666,884

(22) Filed: Nov. 1, 2012

(65) Prior Publication Data

US 2014/0122509 A1    May 1, 2014

(51) Int. Cl.
*G06F 17/30*    (2006.01)

(52) U.S. Cl.
CPC ...... *G06F 17/30023* (2013.01); *G06F 17/3033* (2013.01); *G06F 17/30011* (2013.01); *G06F 17/30424* (2013.01)
USPC ........... 707/769; 707/707; 707/706; 707/708; 707/754

(58) Field of Classification Search
CPC ................ G06F 17/30011; G06F 17/30023; G06F 17/30024; G06F 17/3033
USPC .......... 707/706, 707, 708, 769, 770
See application file for complete search history.

(56) References Cited

U.S. PATENT DOCUMENTS

| | | | | |
|---|---|---|---|---|
| 4,736,308 | A * | 4/1988 | Heckel | 715/781 |
| 5,485,373 | A * | 1/1996 | Davis et al. | 715/205 |
| 5,497,488 | A * | 3/1996 | Akizawa et al. | 1/1 |
| 5,857,185 | A * | 1/1999 | Yamaura | 1/1 |
| 6,738,779 | B1 * | 5/2004 | Shapira | 707/747 |
| 7,013,469 | B2 * | 3/2006 | Smith et al. | 719/328 |
| 7,555,757 | B2 * | 6/2009 | Smith et al. | 719/328 |
| 2005/0240943 | A1 * | 10/2005 | Smith et al. | 719/328 |
| 2005/0246716 | A1 * | 11/2005 | Smith et al. | 719/315 |
| 2008/0270394 | A1 * | 10/2008 | Carson et al. | 707/5 |
| 2012/0084311 | A1 * | 4/2012 | Kawauchi | 707/766 |
| 2012/0254218 | A1 * | 10/2012 | Ali et al. | 707/765 |

OTHER PUBLICATIONS

"DNA Sequence Alignment with SNAP," Apr. 14, 2012, retrieved from https://amplab.cs.berkeley.edu/projects/snap/.
Zaharia, M. et al., "Faster and More Accurate Sequence Alignment with SNAP," Nov. 23, 2011, pp. 1-10 retrieved from http://arxiv.org/pdf/1111.5572v1.pdf.

* cited by examiner

*Primary Examiner* — Frantz Coby
(74) *Attorney, Agent, or Firm* — Zilka-Kotab, PC

(57) ABSTRACT

A system, method, and computer program product are provided for performing a string search. In use, a first string and a second string are identified. Additionally, a string search is performed, utilizing the first string and the second string.

20 Claims, 4 Drawing Sheets

SYSTEM, METHOD, AND COMPUTER PROGRAM PRODUCT FOR PERFORMING A STRING SEARCH

FIELD OF THE INVENTION

The present invention relates to strings, and more particularly to performing string searches.

BACKGROUND

String searches are an important aspect of modern computing technology. For example, string searches may be used to perform web searches, database queries on large portions of text, genome sequencing, etc. However, current techniques for performing string searches have been associated with various limitations.

For example, current methods for performing string searches may utilize a large amount of memory and may take a considerable amount of time and resources to perform. There is thus a need for addressing these and/or other issues associated with the prior art.

SUMMARY

A system, method, and computer program product are provided for performing a string search. In use, a first string and a second string are identified. Additionally, a string search is performed, utilizing the first string and the second string.

DETAILED DESCRIPTION

Figure 1:
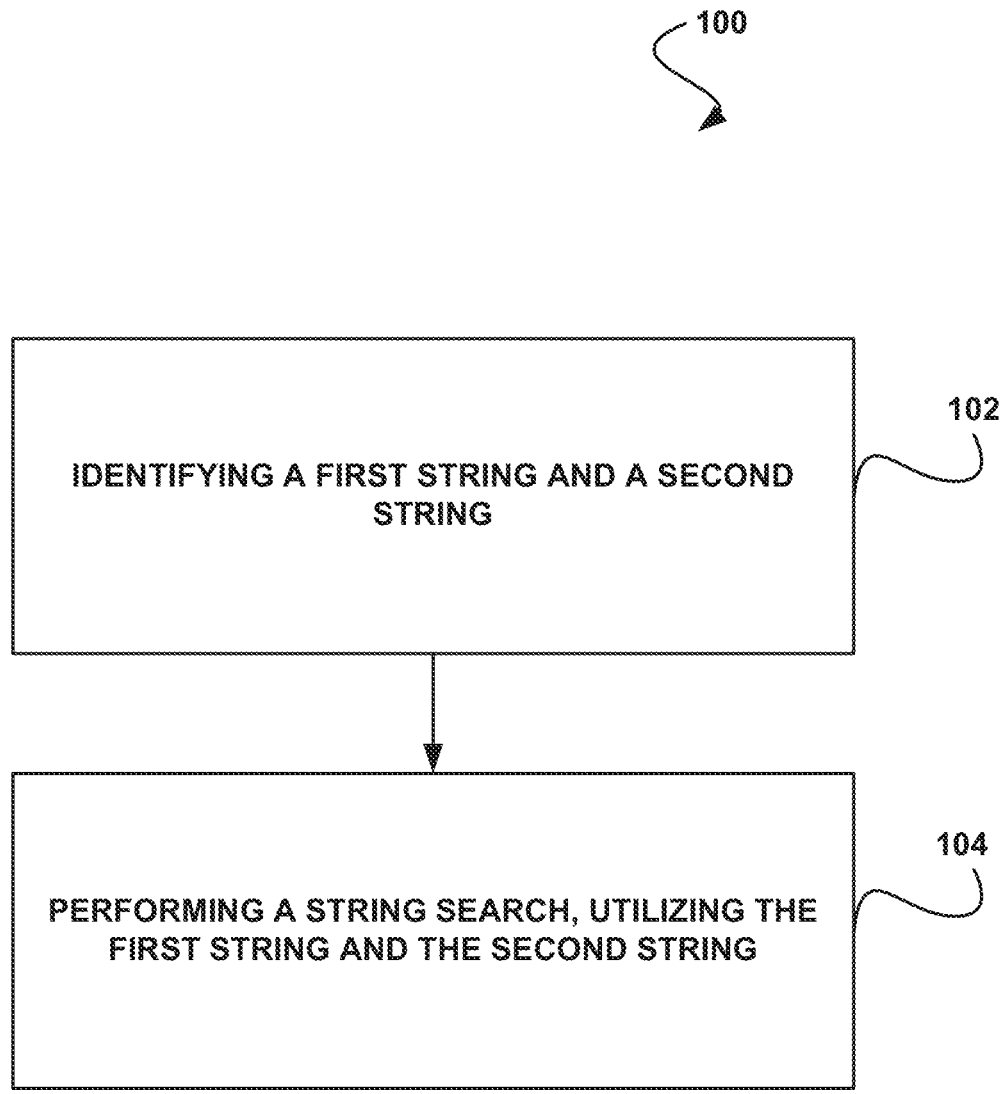
FIG. 1 Shows a method for performing a string search, in accordance with one embodiment.

FIG. 1 shows a method 100 for performing a string search, in accordance with one embodiment. As shown in operation 102, a first string and a second string are identified. In one embodiment, the first string may include a sequence of characters implemented as an array of bytes. In another embodiment, the first string may represent a particular element. For example, the first string may represent the contents of one or more web pages. In another example, the first string may represent a large portion of text.

In yet another example, the first string may represent all or a portion of a genome. For instance, the first string may represent all or a portion of an organism's hereditary information, and may include one or more of genes and non-coding sequences of DNA, RNA, etc. In another embodiment, the first string may represent a reference genome. For example, the first string may represent a digital nucleic acid sequence representative of an exemplary set of genes.

Additionally, in one embodiment, the second string may include a search string. For example, the second string may include a string that is to be searched for within the first string. In another embodiment, the second string may represent all or a portion of a genome. For example, the second string may represent a read (e.g., a portion of a genome that is read from a particular location within the genome, etc.). In yet another embodiment, the second string may represent a portion of a genome separate from the genome represented by the first string. For example, the second string may represent a portion of a sampled genome, and the first string may represent an entirety of a reference genome that is distinct from the sampled genome. In another embodiment, the first string and the second string may be identified by reading the first string and the second string from memory.

Further, as shown in operation 104, a string search is performed, utilizing the first string and the second string. In one embodiment, performing the string search may include performing a search for the second string within the first string to determine whether the first string contains the second string, In another embodiment, performing the string search may include aligning the second string against the first string.

Further still, in one embodiment, performing the string search may include storing the first string within a data structure. For example, performing the string search may include storing the first string in an FM-index. For instance, the first string may be stored in a compressed full-text substring index based on the Burrows-Wheeler transform. In another embodiment, the first string may be partitioned into sub-strings, and such sub-strings may be stored within the FM-index.

Also, in one embodiment, performing the string search may include storing the first string in memory. For example, performing the string search may include storing the first string in on-chip memory, storing the first string in random access memory (RAM), etc. In another embodiment, performing the string search may include dividing the second string into a plurality of portions. For example, performing the string search may include dividing the second string into a plurality of non-overlapping segments.

In addition, in one embodiment, performing the string search may include performing one or more lookups (e.g., searches, etc.) for each of the plurality of portions of the second string within the data structure storing the first string to determine whether each of the plurality of portions of the second string are stored within the data structure, In another embodiment, performing the string search may include determining differences between the first string and the second string, based on the one or more lookups.

Furthermore, in one embodiment, a filter may be used when performing the string search (e.g., before one or more lookups for the second string are performed on the data structure storing the first string, etc.). For example, a Bloom filter (e.g., a space-efficient probabilistic data structure) may be used to test whether the second string is located within the data structure storing the first string. In another example, if the filter indicates that the second string is not located within the data structure storing the first string, the one or more lookups for the second string may not be performed on the data structure.

Further still, in one embodiment, performing the string search may include storing the first string within a hash table (e.g., a data structure that uses a hash function to map keys to associated values, etc.). In another embodiment, performing the string search may include partitioning the hash table storing the first string into a plurality of segments. In yet another embodiment, performing the string search may include classifying each of the plurality of segments. For example, each of the plurality of segments may be sorted such that adjacent segments are more similar with respect to one or more factors than segments that are not adjacent, In another example, each of the plurality of segments may be associated with one of a plurality of predetermined classes.

Also, in one embodiment, performing the string search may include constructing a plurality of new hash tables, where each new hash table is associated with a predetermined class. In another embodiment, performing the string search may include storing all segments associated with a particular class in the new hash table associated with that particular class. In yet another embodiment, the new hash tables may be smaller than the hash table in which the first string was stored.

Additionally, in one embodiment, performing the string search may include partitioning the second string into a plurality of substrings. In another embodiment, performing the string search may include classifying the plurality of substrings. For example, each of the plurality of substrings may be sorted such that adjacent substrings are more similar with respect to one or more factors than substrings that are not adjacent. In another example, each of the plurality of substrings may be associated with one of the plurality of predetermined classes (e.g., the plurality of predetermined classes associated with the new hash tables storing the plurality of segments, etc.). In yet another embodiment, each of the plurality of substrings may be associated with one of the plurality of predetermined classes using a radix sort.

Further, in one embodiment, performing the string search may include loading one of the new hash tables into memory. For example, one of the new hash tables may be loaded into on-chip memory, random access memory (RAM), etc. In another embodiment, performing the string search may include identifying a class associated with the loaded hash table, and identifying one or more substrings associated with that class. In yet another embodiment, performing the string search may include performing one or more lookups (e.g., searches, etc.) for each of the one or more substrings of the second string within the new hash table loaded into memory to determine whether each of the plurality of substrings of the second string are stored within the new hash table.

Further still, in one embodiment, each of a plurality of the new hash tables may be loaded into a memory associated with a distinct processor, and each distinct processor may perform the string search on their particular new hash table, utilizing the one or more substrings associated with the class of the hash table. In this way, the string search may be performed by a plurality of processors in parallel. Additionally, an amount of memory necessary to perform the string search may be reduced. Further, performance may be increased by performing the string search in smaller amounts of faster memory.

More illustrative information will now be set forth regarding various optional architectures and features with which the foregoing framework may or may not be implemented, per the desires of the user. It should be strongly noted that the following information is set forth for illustrative purposes and should not be construed as limiting in any manner. Any of the following features may be optionally incorporated with or without the exclusion of other features described.

Figure 2:
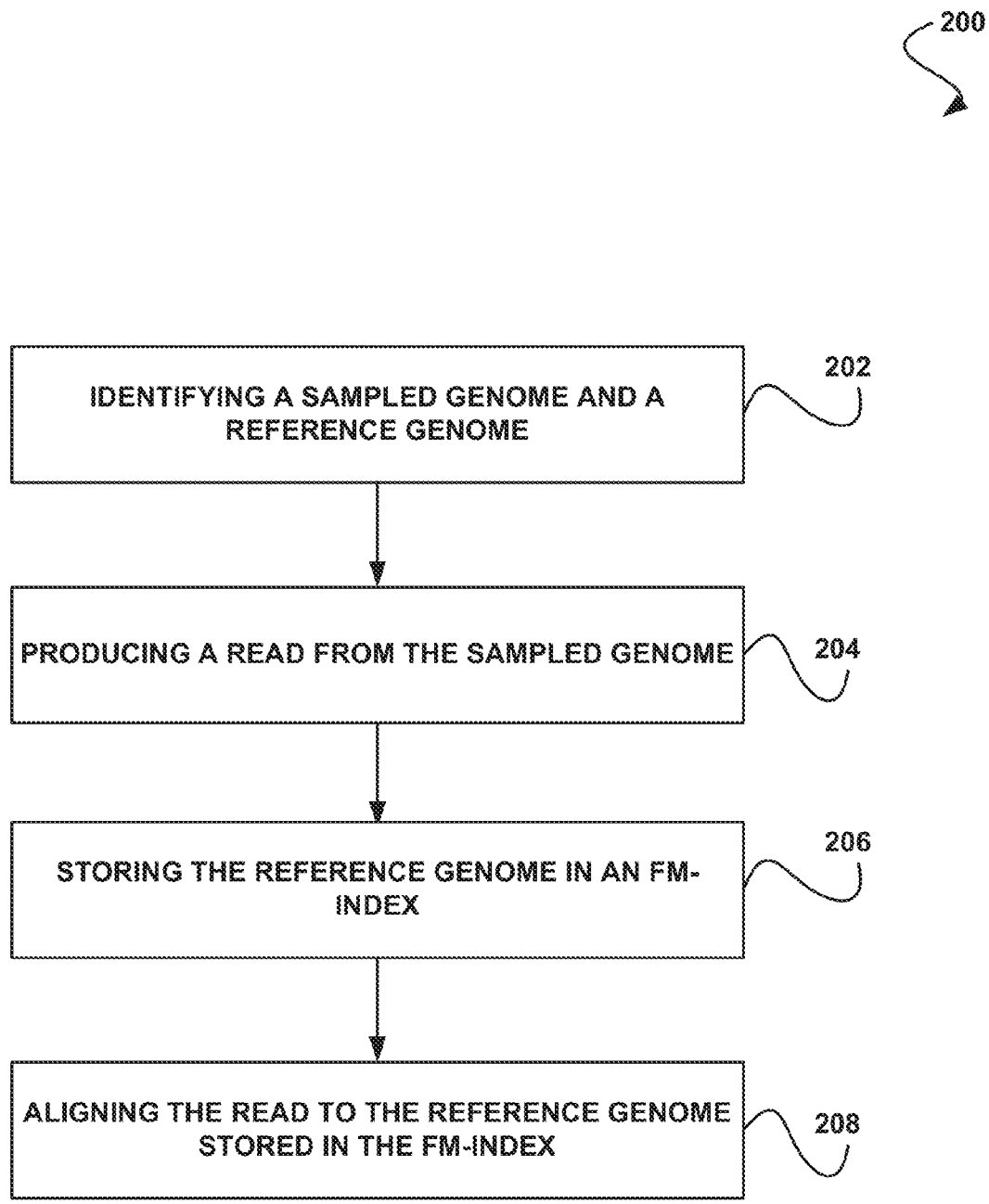
FIG. 2 shows a method for performing genome sequencing utilizing an FM-index, in accordance with another embodiment.

FIG. 2 shows a method 200 for performing genome sequencing utilizing an FM-index, in accordance with another embodiment. As an option, the method 200 may be carried out in the context of the functionality of FIG. 1. Of course, however, the method 200 may be implemented in any desired environment. It should also be noted that the aforementioned definitions may apply during the present description.

As shown in operation 202, a sampled genome and a reference genome are identified. In one embodiment, the reference genome may include a digital nucleic acid sequence representative of an exemplary set of genes, in another embodiment, the sampled genome may include a digital nucleic acid sequence that is sampled for comparison to the reference genome.

Additionally, as shown in operation 204, a read is produced from the sampled genome. In one embodiment, the read may be produced by reading from a location within the sampled genome. Further, as shown in operation 206, the reference genome is stored in an FM-index. In one embodiment, storing the reference genome in an FM index may include determining a plurality of substrings for the reference genome. For example, an FM-index may be built over all possible substrings of m=20 contiguous bases for the reference genome.

Further still, in one embodiment, the reference genome may be stored in an FM-index in memory. For example, the reference genome may be stored in an FM-index in on-chip memory, in random access memory (RAM), etc, Also, as shown in operation 208, the read is aligned to the reference genome stored in the FM-index. In one embodiment, aligning the read to the reference genome may include dividing the read into non-overlapping segments. For example, the read may be divided into n/m non-overlapping segments of in base pairs each.

Additionally, in one embodiment, aligning the read to the reference genome may include performing a lookup for each segment in the FM-index. In this way, the use of the FM-index to store the reference genome may minimize an amount of storage necessary to store the reference genome. Further, a speed by which the reference genome is accessed may be increased.

Further still, in one embodiment, a Bloom filter may be used when aligning the read to the reference genome. For example, a Bloom filter may be used in a lookup to determine whether each segment is located in the FM-index. In another example, if the Bloom filter lookup does not return a result for a segment within the FM-index (e.g., if the Bloom filter lookup is negative for the segment, etc.), an FM-index lookup for that segment may be avoided. In this way, the alignment of the read to the reference genome may be expedited, and may be performed more efficiently.

Also, in one embodiment, the aligning may be performed utilizing a scalable nucleotide alignment program (SNAP). See, for example, "DNA Sequence Alignment with SNAP" (Zaharia et al), which is hereby incorporated by reference in its entirety.

Figure 3:
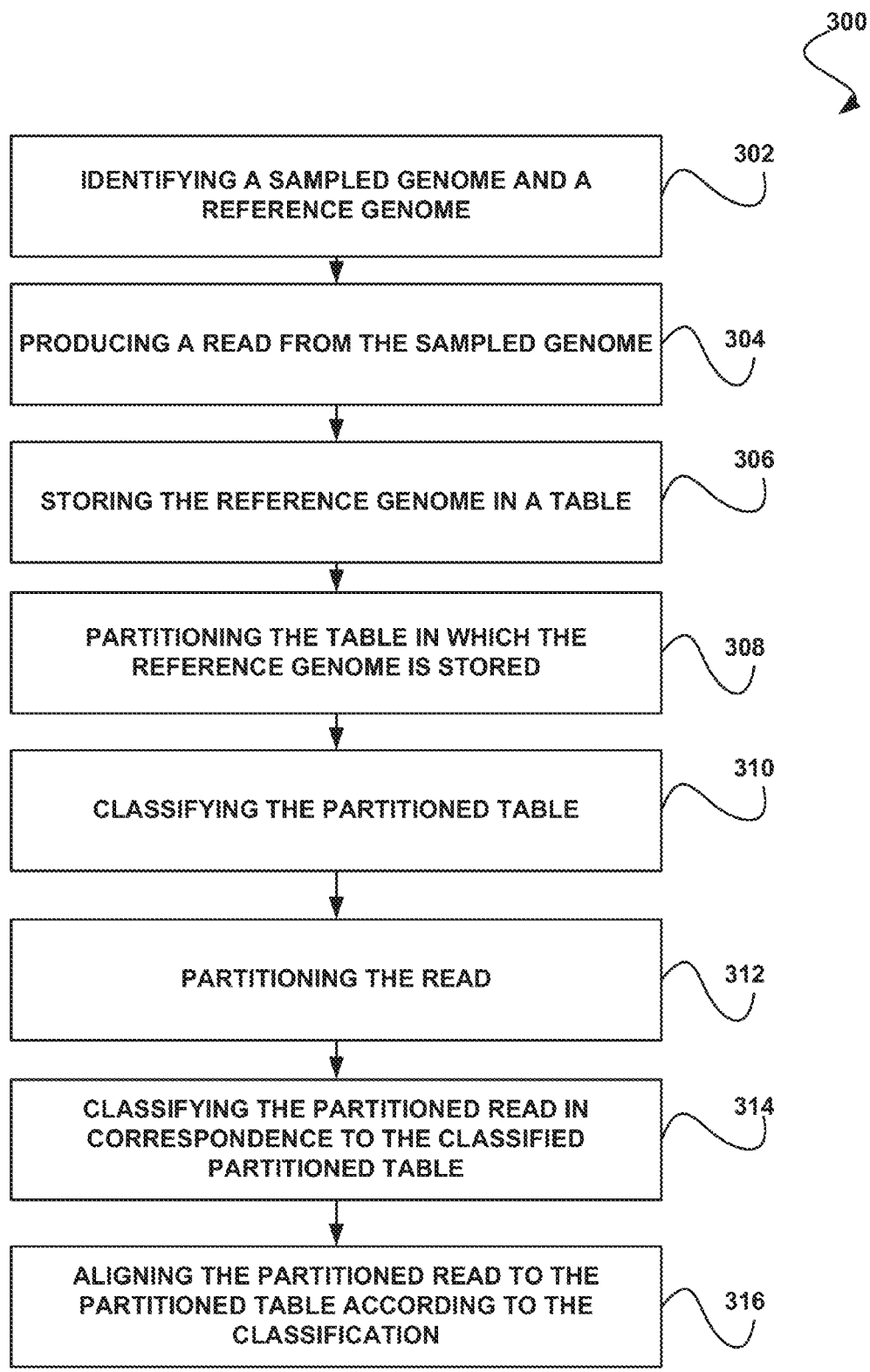
FIG. 3 shows a method for performing genome sequencing utilizing a partitioned table and partitioned read segments, in accordance with another embodiment.

FIG. 3 shows a method 300 for performing genome sequencing utilizing a partitioned table and partitioned read segments, in accordance with another embodiment. As an option, the method 300 may be carried out in the context of the functionality of FIGS. 1-2. Of course, however, the method 300 may be implemented in any desired environment. It should also be noted that the aforementioned definitions may apply during the present description.

As shown in operation 302, a sampled genome and a reference genome are identified. Additionally, as shown in operation 304, a read is produced from the sampled genome. Further, as shown in operation 306, the reference genome is stored in a table. In one embodiment, storing the reference genome in a table may include determining a plurality of substrings for the reference genome. For example, a table (e.g., a hash table, an FM-index, etc.) may be built over all possible substrings of m=20 contiguous bases for the reference genome.

Further still, as shown in operation 308, the table in which the reference genome is stored is partitioned. In one embodiment, partitioning the table may include dividing the table into a plurality of smaller tables. In another embodiment, partitioning the table may include dividing the reference genome into segments.

Also, as shown in operation 310, the partitioned table is classified. In one embodiment, each of the smaller tables may be classified according to a set of p base pairs (e.g., for p in [2, 8], and where the set may be either formed by the first p base pairs or a specific set of p positions, etc.), and 4^p distinct tables may be built, one for each class of segments.

Additionally, as shown in operation 312, the read produced from the sampled genome is partitioned. In one embodiment, partitioning the read may include dividing the read into a plurality of portions. Further, as shown in operation 314, the partitioned read is classified in correspondence to the classified partitioned table. In one embodiment, each of the portions of the read may be classified according to a set of p base pairs (e.g., for p in [2, 8], and where the set may be either formed by the first phase pairs or a specific set of p positions, etc.).

In another embodiment, each partitioned read portion may share a classification with one of the smaller tables, such that each partitioned read has a unique corresponding smaller table. In yet another embodiment, the partitioned read portions may be classified with linear complexity O(N*p) by using a radix sort, where N is the number of segments.

In another embodiment, the partitioned table may include an FM-index, and a position of the segments of the reference genome within the FM-index may be used to classify them. For example, the segments of the reference genome within the FM-index may be partitioned into portions that map to a distinct interval [j, k] in the FM-index, and a separate hash table may be constructed for each portion. In another embodiment, the partitioned read portions may be classified using one or more FM-index traversal steps, until a search range associated with the read portions is small enough to touch only one or two portions.

Further still, as shown in operation 316, the partitioned read is aligned to the partitioned table according to the classification. In one embodiment, each partitioned read portion may be aligned to the corresponding smaller table with which the partitioned read portion shares a classification. In another embodiment, aligning the partitioned read to the partitioned table may include performing a lookup for each partitioned read portion in the corresponding smaller table.

In this way, on processor architectures with low amounts of fast memory, the smaller tables may be loaded into memory one by one. Additionally, on a platform with several processors, each processor may process a distinct classification of partitioned read portions by loading only the corresponding smaller table with which the partitioned read portions share a classification.

Figure 4:
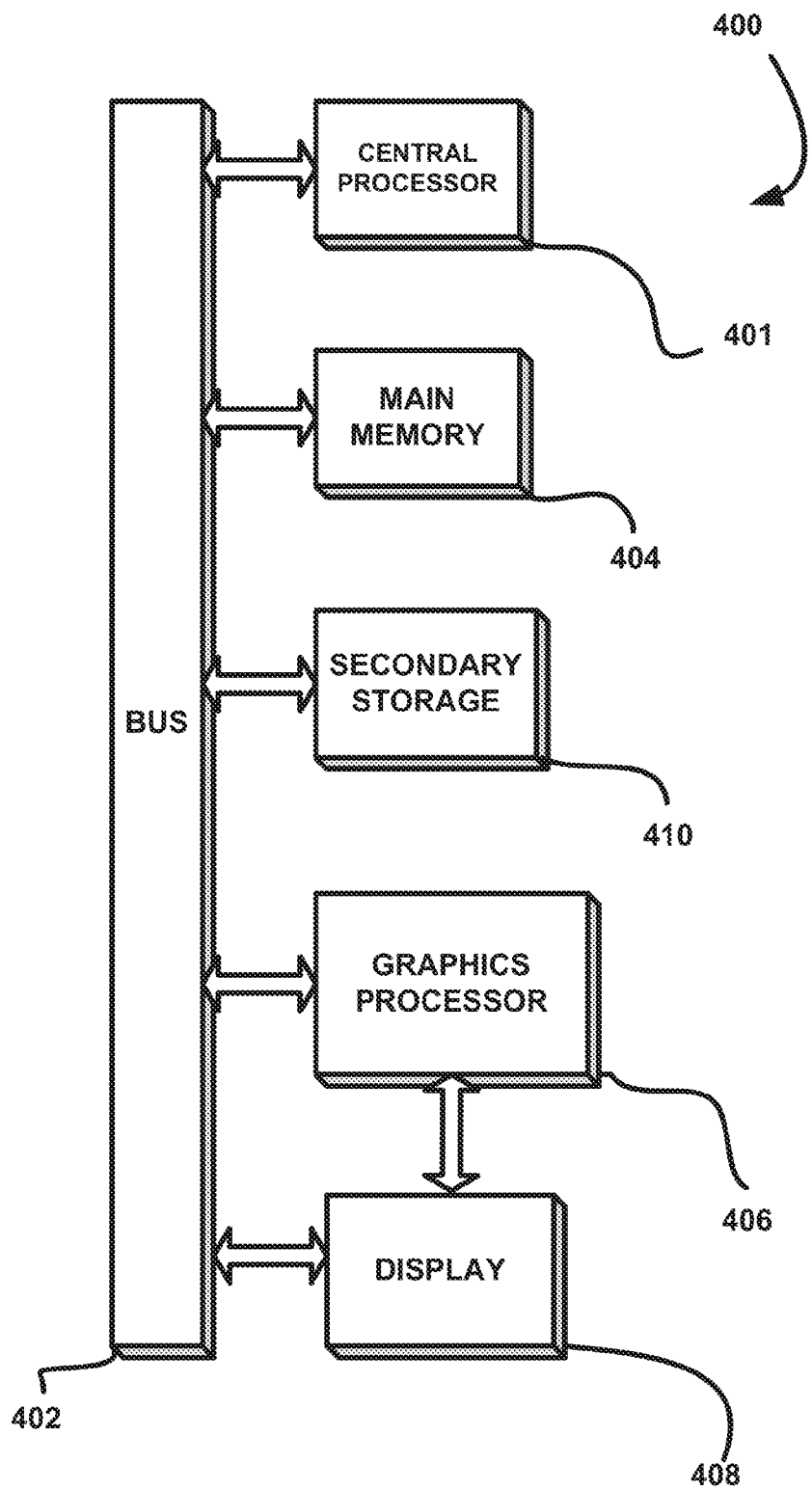
FIG. 4 illustrates an exemplary system in which the various architecture and/or functionality of the various previous embodiments may be implemented.

FIG. 4 illustrates an exemplary system 400 in which the various architecture and/or functionality of the various previous embodiments may be implemented. As shown, a system 400 is provided including at least one host processor 401 which is connected to a communication bus 402. The system 400 also includes a main memory 404. Control logic (software) and data are stored in the main memory 404 which may take the form of random access memory (RAM).

The system 400 also includes a graphics processor 406 and a display 408, i.e. a computer monitor. In one embodiment, the graphics processor 406 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user. The system may also be realized by reconfigurable logic which may include (but is not restricted to) field programmable gate arrays (FPGAs).

The system 400 may also include a secondary storage 410. The secondary storage 410 includes, for example, a hard disk drive and/or a removable storage drive, representing a floppy disk drive, a magnetic tape drive, a compact disk drive, etc. The removable storage drive reads from and/or writes to a removable storage unit in a well known manner.

Computer programs, or computer control logic algorithms, may be stored in the main memory 404 and/or the secondary storage 410. Such computer programs, when executed, enable the system 400 to perform various functions. Memory 404, storage 410 and/or any other storage are possible examples of computer-readable media.

In one embodiment, the architecture and/or functionality of the various previous figures may be implemented in the context of the host processor 401, graphics processor 406, an integrated circuit (not shown) that is capable of at least a portion of the capabilities of both the host processor 401 and the graphics processor 406, a chipset (i.e. a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 400 may take the form of a desktop computer, laptop computer, and/or any other type of logic. Still yet, the system 400 may take the form of various other devices no including, but not limited to a personal digital assistant (PDA) device, a mobile phone device, a television, etc.

Further, while not shown, the system 400 may be coupled to a network [e.g. a telecommunications network, local area network (LAN), wireless network, wide area network (WAN) such as the Internet, peer-to-peer network, cable network, etc.) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:
1. A method, comprising:
identifying a first string and a second string;
storing the first string within a hash table;
partitioning the hash table storing the first string into a plurality of segments;
classifying each segment of the plurality of segments by associating each segment with a predetermined class in a plurality of predetermined classes;
constructing a plurality of new hash tables by storing all segments in the plurality of segments associated with a particular class with a corresponding hash table associated with the particular class; and performing a string search based on the plurality of new hash tables in parallel using a plurality of processors.

2. The method of claim 1, further comprising:
partitioning the second string into a plurality of substrings; and
classifying each substring of the plurality of substrings by associating each substring with a predetermined class.

3. The method of claim 2, further comprising:
loading one of the new hash tables into a memory;
identifying a class associated with the hash table loaded into the memory; and
identifying one or more substrings in the plurality of substrings associated with that class.

4. The method of claim 3, wherein performing the string search comprises performing one or more lookups for each of the one or more substrings within the hash table loaded into the memory to determine whether each of the one or more substrings is stored within the new hash table.

5. The method of claim 1, wherein each hash table in the plurality of new hash tables is loaded into a memory associated with a distinct processor in the plurality of processors.

6. The method of claim 5, wherein each distinct processor in the plurality of processors performs a portion of the string search on a corresponding hash table associated with that distinct processor.

7. The method of claim 1, wherein each of the hash tables is stored in random access memory (RAM).

8. The method of claim 1, wherein the first string comprises a reference genome and the second string comprises a sampled genome.

9. The method of claim 1, wherein a filter is used when performing the string search.

10. The method of claim 9, wherein the filter comprises a Bloom filter.

11. A computer program product embodied on a non-transitory computer readable medium, comprising:
code for identifying a first string and a second string;
code for storing the first string within a hash table;
code for partitioning the hash table storing the first string into a plurality of segments;
code for classifying each segment of the plurality of segments by associating each segment with a predetermined class in a plurality of predetermined classes;
code for constructing a plurality of new hash tables by storing all segments in the plurality of segments associated with a particular class with a corresponding hash table associated with the particular class; and
code for performing a string search based on the plurality of new hash tables in parallel using a plurality of processors.

12. The computer program product of claim 11, further comprising:
code for partitioning the second string into a plurality of substrings; and
code for classifying each substring of the plurality of substrings by associating each substring with a predetermined class.

13. The computer program product of claim 12, further comprising:
code for loading one of the new hash tables into a memory;
code for identifying a class associated with the hash table loaded into the memory; and
code for identifying one or more substrings in the plurality of substrings associated with that class.

14. The computer program product of claim 13, wherein performing the string search comprises performing one or more lookups for each of the one or more substrings within the hash table loaded into the memory to determine whether each of the one or more substrings is stored within the new hash table.

15. A system, comprising:
a memory; and
a plurality of processors coupled to the memory and configured to:
identify a first string and a second string;
store the first string within a hash table;
partition the hash table storing the first string into a plurality of segments;
classify each segment of the plurality of segments by associating each segment with a predetermined class in a plurality of predetermined classes;
construct a plurality of new hash tables by storing all segments in the plurality of segments associated with a particular class with a corresponding hash table associated with the particular class; and
perform a string search based on the plurality of new hash tables in parallel using the plurality of processors.

16. The system of claim 15, wherein the plurality of processors is further configured to:
partition the second string into a plurality of substrings; and
classify each substring of the plurality of substrings by associating each substring with a predetermined class.

17. The system of claim 16, wherein the plurality of processors is further configured to:
load one of the new hash tables into the memory;
identify a class associated with the hash table loaded into the memory; and
identify one or more substrings in the plurality of substrings associated with that class.

18. The system of claim 17, wherein performing the string search comprises performing one or more lookups for each of the one or more substrings within the hash table loaded into the memory to determine whether each of the one or more substrings is stored within the new hash table.

19. The system of claim 15, wherein the plurality of processors is coupled to the memory via a bus.

20. The system of claim 15, wherein the memory comprises a random access memory (RAM) and each of the hash tables is stored in the RAM.

* * * * *